US012708118B1

(12) United States Patent
Burton

(10) Patent No.: US 12,708,118 B1
(45) Date of Patent: Aug. 18, 2026

(54) COMPOSITIONS AND METHODS FOR DECONTAMINATION

(71) Applicant: National Technology & Engineering Solutions of Sandia, LLC, Albuquerque, NM (US)

(72) Inventor: Patrick D. Burton, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 460 days.

(21) Appl. No.: 18/388,293

(22) Filed: Nov. 9, 2023

(51) Int. Cl.
*A01N 59/00* (2006.01)
*A01N 25/02* (2006.01)
*A01P 1/00* (2006.01)
*A61L 2/186* (2026.01)

(52) U.S. Cl.
CPC ............. *A01N 59/00* (2013.01); *A01N 25/02* (2013.01); *A01P 1/00* (2021.08); *A61L 2/186* (2013.01)

(58) Field of Classification Search
CPC ............ A01N 59/00; A01N 25/02; A01P 1/00
See application file for complete search history.

(56) References Cited

U.S. PATENT DOCUMENTS 6,566,574 B1 5/2003 Tadros et al.
7,662,759 B1 2/2010 Tucker et al.
7,750,199 B1 7/2010 Tucker
7,850,865 B1 12/2010 Tucker et al.
8,022,265 B2 9/2011 Tucker
8,741,174 B1 6/2014 Tucker
11,077,327 B1 8/2021 Sava Gallis et al.
2021/0214307 A1* 7/2021 Back .................... C07C 215/08

FOREIGN PATENT DOCUMENTS

CN 101979490 A * 2/2011

OTHER PUBLICATIONS

CN101979490A; machine translation, pp. 1-3 (Year: 2011).*

* cited by examiner

*Primary Examiner* — Andrew S Rosenthal
(74) *Attorney, Agent, or Firm* — Daniel J. Jenkins; Kenneth Paul McNeill

(57) ABSTRACT

The disclosure relates to compositions, methods for making the compositions, and methods for decontaminating substrates wherein the decontaminating compositions comprise a mixture of a peroxide solution and a surfactant composition, wherein (i) the surfactant composition comprises: (a) from about 20% to about 40% xanthan gum, (b) from about 10% to about 25% levulinic acid, (c) from about 32% to about 63% ethyl lactate, and (d) from about 3% to about 7% polyoxyethylene (20) sorbitan monooleate, wherein all weights are relative to the total weight of the surfactant composition, (ii) the peroxide solution comprises from about 1% to about 12% hydrogen peroxide, and the mixture comprises from about 0.001 g to about 10 g of the surfactant composition per liter of the peroxide solution.

20 Claims, 2 Drawing Sheets

COMPOSITIONS AND METHODS FOR DECONTAMINATION

STATEMENT REGARDING RESEARCH OR DEVELOPMENT

Described examples were made with Government support under Contract No. DE-NA0003525 awarded by the United States Department of Energy/National Nuclear Security Administration. The U.S. Government has certain rights in the invention.

TECHNICAL FIELD

The present disclosure relates to compositions and methods for decontaminating surfaces.

BACKGROUND

Compositions for decontamination and/or routine cleaning can be used to sanitize and/or clean surfaces. A decontamination or cleansing product should effectively neutralize pathogens without causing damage to non-targeted flora or substrates, either at the time of use or after bioaccumulation. It has been observed that broad-spectrum chlorine-based oxidizers or quaternary amine disinfectants can react with a treated substrate and leave undesirable residue. In addition to such residue being unsightly and therefore generally disfavored, such residue may damage the treated substrate and/or may retain harsh chemicals that pose an environmental risk and/or risk to individuals who come into contact with the residue. As such, there is a need for decontamination and cleansing compositions that are active when and where needed, but that leave little to no harmful residue, and are less toxic and/or corrosive.

SUMMARY

The disclosure relates, in various embodiments, to compositions and methods for decontaminating substrates and materials, and methods of making such compositions.

The compositions may include (a) a hydrogen peroxide; (b) at least one nonionic surfactant; (c) at least one viscosity modifier; and (d) at least one solvent. In an embodiment, the decontaminating compositions comprise a mixture of a peroxide solution and a surfactant composition, wherein (i) the surfactant composition comprises: (a) from about 20% to about 40% xanthan gum, (b) from about 10% to about 25% levulinic acid, (c) from about 32% to about 63% ethyl lactate, and (d) from about 3% to about 7% polyoxyethylene (20) sorbitan monooleate, wherein all weights are relative to the total weight of the surfactant composition, (ii) the peroxide solution comprises from about 1% to about 12% hydrogen peroxide, and the mixture comprises from about 0.001 g to about 10 g of the surfactant composition per liter of the peroxide solution.

In an embodiment, the surfactant composition comprises from about 25% to about 35% by weight xanthan gum, relative to the total weight of the surfactant composition.

In another embodiment, the surfactant composition comprises from about 15% to about 23% by weight levulinic acid, relative to the total weight of the surfactant composition.

In another embodiment, the surfactant composition comprises from about 40% to about 50% by weight ethyl lactate, relative to the total weight of the surfactant composition.

In another embodiment, the surfactant composition comprises from about 4% to about 6% by weight polyoxyethylene (20) sorbitan monooleate, relative to the total weight of the surfactant composition.

In another embodiment, the pH of the mixture is basic.

In a further embodiment, the decontaminating composition comprises (i) a surfactant composition comprising: (a) from about 25% to about 35% xanthan gum, (b) from about 15% to about 23% levulinic acid, (c) from about 40% to about 50% ethyl lactate, and (d) from about 4% to about 6% polyoxyethylene (20) sorbitan monooleate, wherein all weights are relative to the total weight of the surfactant composition, (ii) and a peroxide solution comprising from about 2% to about 8% hydrogen peroxide, wherein the mixture comprises from about 0.1 g to about 4 g of the surfactant composition per liter of the peroxide solution.

The methods of making a decontaminating composition may comprise mixing a peroxide solution with a surfactant composition.

The methods of decontaminating a substrate may comprise: (A) mixing a peroxide solution with a surfactant composition, and (B) applying the mixture to a substrate.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to limit the scope, the embodiments will be described and explained with additional specificity and detail through the use of the drawings below.

DETAILED DESCRIPTION OF THE EMBODIMENTS

Figure 1:
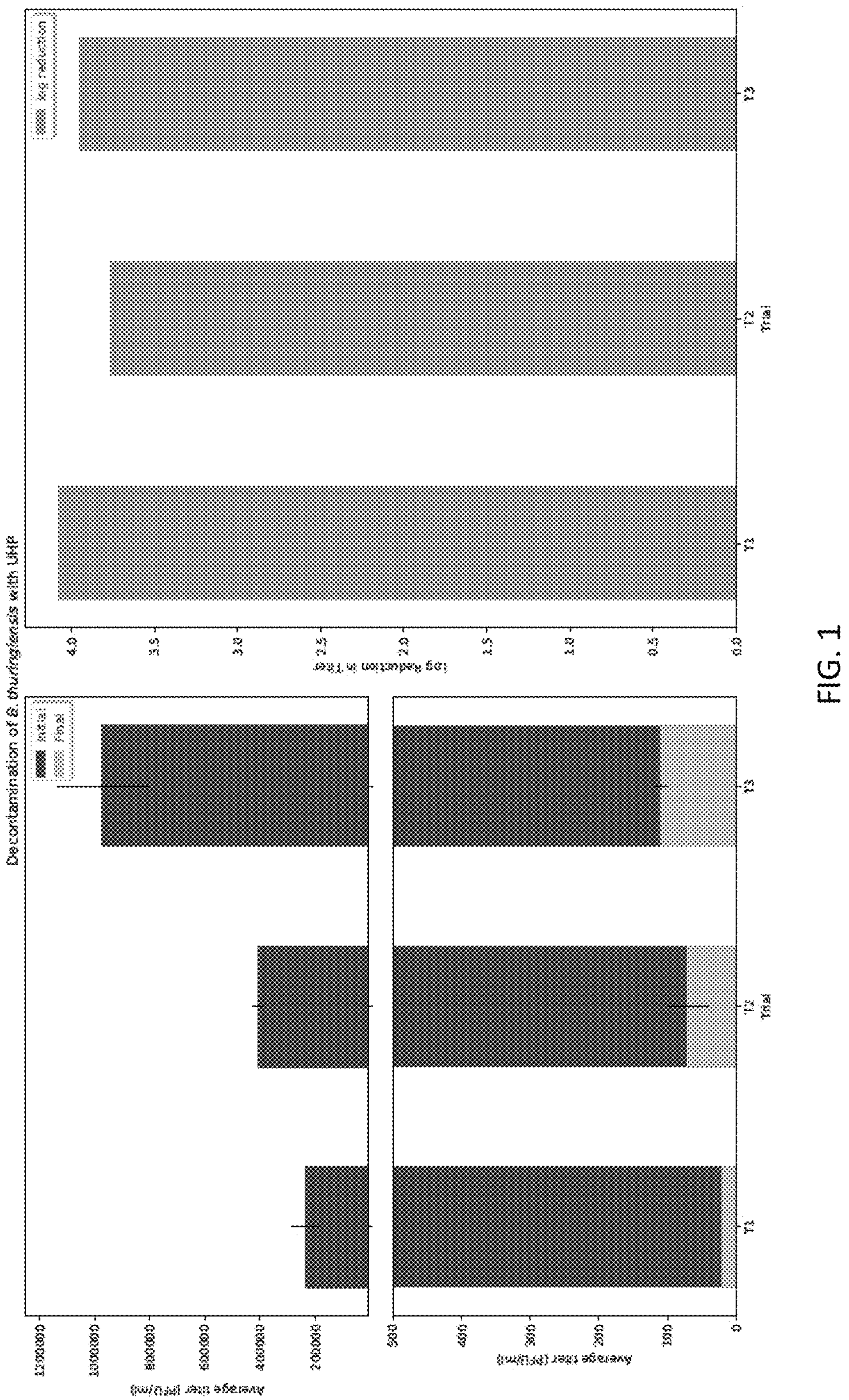
FIG. 1 shows diagrams illustrating titer and log reduction of *B. thuringiensis* after contact with UHP-based compositions.

The disclosure relates to compositions for decontaminating substrates, comprising (a) at least one of hydrogen peroxide, salts thereof, or percarbonate salts thereof; (b) at least one nonionic surfactant; (c) at least one viscosity modifier; and (d) at least one solvent. In various embodiments, the compositions surprisingly leave little to no residue on the surface of the treated substrates and are considered to be environmentally and user-friendly. The disclosure also relates to methods of making and using the compositions for decontamination of substrates.

In an embodiment, compositions according to the present disclosure act as surfactant solutions and can leave minimal residue on applied surfaces. In a further embodiment, compositions of the disclosure comprise low toxicity ingredients.

I. Decontaminating Compositions

In various embodiments, compositions according to the disclosure comprise a mixture of a peroxide solution and a surfactant composition. The surfactant composition comprises: (a) from about 20% to about 40% xanthan gum, (b) from about 10% to about 25% levulinic acid, (c) from about 32% to about 63% ethyl lactate, and (d) from about 3% to about 7% polyoxyethylene (20) sorbitan monooleate, wherein all weights are relative to the total weight of the surfactant composition. The peroxide solution comprises from about 1% to about 12% hydrogen peroxide. The mixture comprises from about 0.001 g to about 10 g of the surfactant composition per liter of the peroxide solution.

In an embodiment, the composition is a decontaminating composition. “Decontaminating” (and “decontaminant”) refers to inactivating, killing or removing undesired microorganisms such as pathogens. Decontamination comprises, but is not limited to, disinfection, high-level disinfections (HLD), and sterilizations. Decontamination may include log reductions in the number of undesirable living microorganisms of at least about 4, or at least about 5, or at least about 6.

Peroxide Solutions

Hydrogen Peroxide

Compositions according to the disclosure comprise hydrogen peroxide ($H_2O_2$). However, it may in some embodiments be useful to choose a hydrogen peroxide generating system, which can generate hydrogen peroxide in situ, in addition to or instead of hydrogen peroxide. For example, useful hydrogen peroxide generating system may be chosen from salts of hydrogen peroxide such as percarbonate salts, e.g., sodium percarbonate, urea hydrogen peroxide, polymeric complexes, or mixtures of two or more thereof that can release hydrogen peroxide such as polyvinylpyrrolidone/$H_2O_2$ and other polymeric complexes described in U.S. Pat. Nos. 5,008,093; 3,376,110; and 5,183,901, and/or oxidases which produce hydrogen peroxide, such as glucose oxidase or uricase.

It is contemplated that combinations of two or more different hydrogen peroxide generating systems, or combinations of hydrogen peroxide with one or more hydrogen peroxide generating systems, can be chosen.

In some embodiments, however, only hydrogen peroxide is used, and the compositions do not contain any other hydrogen peroxide generating systems.

In various embodiments, the hydrogen peroxide component may be in the form of a dry powder, an emulsion, or a solution. It may, for example, be advantageous to use urea hydrogen peroxide in the form of a powder, or hydrogen peroxide in the form of an aqueous solution.

Typically, the compositions comprise no more than about 15% hydrogen peroxide, for example no more than about 12%, no more than about 10%, no more than about 9%, or no more than about 8% hydrogen peroxide by weight, relative to the total weight of the peroxide solution. For example, in various embodiments, the peroxide solutions comprise a total hydrogen peroxide content ranging from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, or from about 8% to about 9% by weight, relative to the total weight of the surfactant composition. In some embodiments, the compositions comprise a total hydrogen peroxide content ranging from about 3.5% to about 8.5%, such as from about 4.5% to about 8.5%, from about 5.5% to about 8.5%, from about 6.5% to about 8.5%, from about 7.5% to about 8.5%, from about 3.5% to about 8%, such as from about 4.5% to about 8%, from about 5.5% to about 8%, from about 6.5% to about 8%, from about 7.5% to about 8%, from about 3.5% to about 7.5%, from about 4.5% to about 7.5%, from about 5.5% to about 7.5%, from about 6.5% to about 7.5%, from about 7% to about 7.5%, or from about 7.75% to about 8.25% by weight, relative to the total weight of the peroxide solution. In certain embodiments, the concentrations are relative to the total weight of the decontaminating composition.

In embodiments where a hydrogen peroxide generating agent is used, it is within the ability of a skilled person to choose an amount of hydrogen peroxide generating agent(s) to provide a hydrogen content within the aforementioned ranges. For example, a skilled person would know that sodium percarbonate contains about 32.5% hydrogen peroxide, and therefore would add an appropriate amount of sodium percarbonate to achieve the desired hydrogen peroxide content. By way of non-limiting example, if sodium percarbonate was used as a hydrogen peroxide generating agent and a hydrogen peroxide content of approximately 5% was desired, the skilled person would know to use approximately 15% sodium percarbonate.

In some embodiments, the hydrogen peroxide component comprises, consists essentially of, or consists of hydrogen peroxide, urea hydrogen peroxide, sodium percarbonate, or a mixture of two or more thereof, which are used in amounts providing a hydrogen peroxide content in any of the disclosed ranges.

Surfactant Compositions

Nonionic Surfactants

Compositions according to the disclosure comprise at least one nonionic surfactant. Useful and non-limiting examples of nonionic surfactants include esters of fatty acids, which may be optionally ethoxylated, propoxylated, or glycerolated; monoglyceryl or polyglyceryl esters of fatty acids; fatty alcohol ethoxylates; or mixtures of two or more thereof.

Useful examples of optionally ethoxylated, propoxylated, or glycerolated fatty acid esters include, but are not limited to, polyoxyethylenated C8-C30 fatty acid esters (e.g., C12-C18) of sorbitan, such as lauric, myristic, oleic, or stearic acids of sorbitan, for example polyoxyethylenated sorbitan monolaurate (4 EO) (Polysorbate-21), polyoxyethylenated sorbitan monolaurate (20 EO) (Polysorbate-20), polyoxyethylenated sorbitan monopalmitate (20 EO), (Polysorbate-40), polyoxyethylenated sorbitan monostearate (20 EO) (Polysorbate-60), polyoxyethylenated sorbitan monostearate (4 EO) (Polysorbate-61), or polyoxyethylenated sorbitan monooleate (20 EO) (Polysorbate-80). In some embodiments, the compositions comprise at least one surfactant chosen from polyoxyethylenated alkyl esters of sorbitan with a number of ethylene oxide (EO) units ranging from 0 to 100. In some embodiments, the nonionic surfactant comprises, consists essentially of, or consists of polyoxyethylene (80) sorbitan monooleate, available for example under the name TWEEN 80®.

Exemplary and nonlimiting monoglyceryl esters of fatty acids include glyceryl oleate, glyceryl laurate, glyceryl stearate, glyceryl ricinoleate, or mixtures of two or more thereof.

Useful polyglyceryl esters of fatty acids include, for example, polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, or polyglyceryl-10 stearate.

The nonionic surfactants/emulsifiers may also be chosen from alcohols and alpha-diols, these compounds being polyethoxylated and/or polypropoxylated and/or polyglycerolated, the number of ethylene oxide and/or propylene oxide groups possibly ranging from 2 to 100, and the number of glycerol groups possibly ranging from 2 to 30; these compounds comprising at least one fatty chain comprising from 8 to 30 carbon atoms such as from 16 to 30 carbon atoms.

By way of example, fatty alcohol ethoxylates may be chosen from C12-C18 fatty alcohols such as polyoxyethylenated lauryl alcohol, cetyl alcohol, myristyl alcohol, and stearyl alcohol having from 2 to 30 mol of ethylene oxide, including cetyl alcohol polyoxyethylenated with 2 EO (Ceteth-2), cetyl alcohol polyoxyethylenated with 6 EO (Ceteth-6), cetyl alcohol polyoxyethylenated with 10 EO (Ceteth-10), cetyl alcohol polyoxyethylenated with 20 EO (Ceteth-20), cetyl alcohol polyoxyethylenated with 24 EO (Ceteth-24), lauryl alcohol polyoxyethylenated with 2 EO (Laureth-2), lauryl alcohol polyoxyethylenated with 3 EO (Laureth-3), lauryl alcohol polyoxyethylenated with 4 EO (Laureth-4), lauryl alcohol polyoxyethylenated with 7 EO (Laureth-7), lauryl alcohol polyoxyethylenated with 9 EO (Laureth-9), lauryl alcohol polyoxyethylenated with 10 EO (Laureth-10), lauryl alcohol polyoxyethylenated with 12 EO (Laureth-12), lauryl alcohol polyoxyethylenated with 21 EO (Laureth-21), lauryl alcohol polyoxyethylenated with 23 EO (Laureth-23), stearyl alcohol polyoxyethylenated with 2 EO (Steareth-2), stearyl alcohol polyoxyethylenated with 10 EO (Steareth-10), stearyl alcohol polyoxyethylenated with 20 EO (Steareth-20), or stearyl alcohol polyoxyethylenated with 21 EO (Steareth-21).

In various embodiments, the compositions comprise at least one surfactant chosen from polyoxyethylenated alkyl esters of sorbitan such as polyoxyethylene (80) sorbitan monooleate, monoglyceride surfactants such as glyceryl monocaprate, glyceryl monooleate, glyceryl monolaurate, or diglyceride surfactants such as glyceryl diacetate.

In various embodiments, the compositions comprise a total amount of nonionic surfactants up to about 2%, up to about 1.5%, up to about 1%, up to about 0.75%, up to about 0.5%, up to about 0.25%, or up to about 0.1%, or ranging from about ranging from about 0.001% to about 10%, from about 0.004% to about 9%, from about 0.005% to about 8%, from about 0.006% to about 7%, from about 0.007% to about 6%, from about 0.008% to about 5%, from about 0.009% to about 5%, from about 0.01% to about 3%, from about 0.02% to about 10%, from about 0.03% to about 9%, from about 0.04% to about 8%, from about 0.05% to about 7%, from about 0.06% to about 6%, from about 0.07% to about 5%, from about 0.08% to about 4%, from about 0.09% to about 3%, from about 0.1% to about 15%, from about 0.25% to about 12%, from about 0.5% to about 10%, from about 0.75% to about 9%, from about 1% to about 8%, from about 1.25% to about 7%, from about 1.5% to about 6%, or from about 2% to about 5% by weight, relative to the total weight of the surfactant composition, including all ranges and subranges thereof. In some embodiments, the compositions comprise a total amount of non-ionic surfactants ranging from about 0.001% to about 5%, such as from about 0.01% to about 5%, or from about 0.05% to about 4% by weight, relative to the total weight of the surfactant composition. In an embodiment, the nonionic surfactant is comprising polyoxyethylene (20) sorbitan monooleate. In an embodiment, the nonionic surfactant is polyoxyethylene (20) sorbitan monooleate.

In some embodiments, the compositions are free or essentially free of anionic, cationic surfactants, and/or zwitterionic surfactants.

Viscosity Modifiers

The compositions of the disclosure optionally comprise at least one viscosity modifier. A slightly thickened solution is advantageous for adhesion to a treated surface, thus maximizing the contact time with the decontamination or cleansing composition. Useful and non-limiting examples of viscosity modifiers include, for example, water-soluble synthetic polymers, sugar alcohols, and natural polysaccharides.

In various embodiments, useful viscosity modifiers include sorbitol, mannitol, maltitol, hydrogenated starch hydrolysate (HSH), xylitol, lactitol monohydrate, anhydrous isomalt, erythritol, zeolytes, precipitated silica, fumed silica, dendritic salt, sea salt, polyethylene glycol, urea, sodium gluconate, potassium gluconate, polyols, xanthan gum, polydextrose, guar gum, agar, carrageenan, sodium alginate, caseinate, celluloses, and other natural and synthetic polysaccharide polymers, non-ionic polymers such as 2-hydroxylethylcellulose that can turn the composition into a flowable cream. Suitable celluloses include: Carboxymethyl Cellulose (CMC), Polyanionic Cellulose (PAC), hydroxymethylcellulose, hydroxypropylcellulose, and hydroxypropylmethyl cellulose (HPMC).

In various exemplary embodiments, the total amount of viscosity modifiers may vary, and may typically range from about 5% to about 55%, such as from about 10% to about 50%, from about 15% to about 45%, from about 20% to about 40%, from about 25% to about 35%, from about 28% to about 32%, relative to the total weight of the surfactant composition, including all ranges and subranges thereof. In an embodiment, the viscosity modifier comprises xanthan gum. In an embodiment, the viscosity modifier is xanthan gum.

In some embodiments, the total amount of viscosity modifiers may range from about 1% to about 50%, such as from about 2% to about 45%, from about 4% to about 40%, or from about 6% to about 35%, or may be from about 8% to about 30%, from about 10% to about 25%, from about 15% to about 20% by weight, relative to the total weight of the surfactant composition, including all ranges and subranges using any of the foregoing as upper or lower limits. In an embodiment, the viscosity modifier comprises levulinic acid. In an embodiment, the viscosity modifier is levulinic acid.

Solvents

Compositions according to the disclosure, including the peroxide solution and the surfactant composition, comprise at least one solvent. Solvents that can be used include water, non-aqueous solvents, or combinations thereof. Useful and non-limiting examples of non-aqueous solvents that may be chosen include alcohols such as C1-C4 alcohols, fatty alcohols, fatty ethers, fatty esters, polyols, glycols, synthetic or natural oils, liposomes, laminar lipid materials, or combinations of two or more thereof.

By way of example only, useful solvents include hydrocarbon-based oils which comprise, consist essentially of, or consist of carbon and hydrogen atoms, and optionally containing oxygen and/or nitrogen atoms and/or alcohol, ester, ether, carboxylic acid, amine and/or amide groups, but not containing any silicon or fluorine atoms. The hydrocarbon-based oils may be chosen from, for example, C8-C14 hydrocarbon-based oils such as branched C8-C14 alkanes for instance isododecane or isodecane, and linear alkanes for instance n-dodecane and n-tetradecane, and short-chain esters (for example containing from 3 to 8 carbon atoms in total) such as ethyl acetate, methyl acetate, propyl acetate and n-butyl acetate; hydrocarbon-based oils of plant origin such as wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; polyols such as glycerol, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (octylene glycol), 1,2-hexanediol, 1,2-pentanediol, and 4-methyl-1,2-pentanediol; alkyl alcohols having 1 to 4 carbon atoms, such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-isopropyl ether, diethylene glycol mono-isopropyl ether, ethylene glycol mono-n-butyl ether, ethylene glycol mono-tert-butyl ether, diethylene glycol mono-tert-butyl ether, 1-methyl-1-methoxybutanol, propylene glycol monomethyl ether, propylene glycol monoethyl ether, propylene glycol mono-tert-butyl ether, propylene glycol mono-n-propyl ether, propylene glycol mono-isopropyl ether, dipropylene glycol monomethyl ether, dipropylene glycol monoethyl ether, dipropylene glycol mono-n-propyl ether, dipropylene glycol mono-isopropyl ether; as ethylene glycol diacetate, propylene glycol monomethyl ether acetate, methyl acetate, dimethyl glutarate, diethylene glycol monoethyl ether acetate, glycerol acetate (monoacetin), glycerol diacetate (diacetin), glycerol triacetate (triacetin), acetylcholine chloride, 4-cyanobenzoic acid, or propylene glycol diacetate, as well as mixtures of two or more thereof. In some embodiments, the compositions comprise at least one solvent chosen from water, ethyl acetate, ethyl lactate, and glycerol diacetate, as well as mixtures of two or more thereof.

In various embodiments, compositions according to the disclosure may be prepared by diluting a pre-formulated product, which may, for example, be in the form of a concentrated solution, emulsion, or dry powder, with a solvent before use.

In an embodiment, the compositions can be in concentrated forms. A dry solid carrier for hydrogen peroxide can reduce the volume of water required to transport the decontaminant to the point of use. Dry powders including hydrogen peroxide chemically bound to either urea or sodium carbonate are suitable for shelf storage, and they can release hydrogen peroxide upon dissolution in water. The slurry form of the compositions of the disclosure can achieve 1.6 g slurry corresponding to one liter completed decontaminant solution upon dissolution in water. As such, the requisite water can be supplied on site, thus enabling three orders of magnitude reduction in transportation logistics.

The pre-formulated product may, in various embodiments, be added directly to a solvent or solvent mixture in any manner, and mixed or combined to prepare a composition. By way of example only, the solvent composition to which a pre-formulated product may be added or may include, but is not limited to, water, propylene glycol diacetate, isobutanol, tripropylene glycol methyl ether, ethyl lactate, hexylene glycol, diethylene glycol methyl ether, propylene glycol, water, or mixtures of two or more thereof.

In some embodiments, the total amount of solvent in the surfactant composition may range from about 10% to about 85%, such as from about 15% to about 80%, from about 20% to about 75%, from about 25% to about 70%, from about 30% to about 65%, from about 35% to about 60%, from about 40% to about 55%, from about 45% to about 50%, relative to the total weight of the surfactant composition, including all ranges and subranges using any of the foregoing as upper or lower limits. In an embodiment, the solvent in the surfactant comprises ethyl lactate. In an embodiment, the viscosity modifier is ethyl lactate.

Other Ingredients

Auxiliary Components

In various embodiments, the compositions may optionally include one or more auxiliary components chosen from water-soluble peroxide activators such as bicarbonate salts; foam stabilizers such as n-dodecanol, n-tetradecanol, n-tridecanol; or n-hexadecanol. Optionally, the compositions may further include fatty alcohols such as alcohols having 8-20 carbon atoms per molecule, such as 1-dodecanol, 1-tridecanol, hexadecanol, and 1-tetradecanol.

pH Adjusters

In various embodiments, the pH of the compositions is basic, and in some embodiments the pH may be mildly basic. For example, the pH of the composition may be above 7, such as from about 7.5 to about 11, about 8 to about 10.5, about 8.5 to about 11, about 9 to about 10.5, about 9.5 to about 10, or any range therebetween using any of the disclosed pHs as upper or lower endpoints.

It may, therefore, be advantageous in some embodiments to include one or more pH adjusters. By way of example, one or more carboxylic acids or salts thereof may be chosen from levulinic acid, acetic acid, lactic acid, or citric acid, or salts of any of the foregoing. As further examples, sodium bicarbonate or carbonate salts, ammonium bicarbonate or carbonate salts, sodium or potassium borate salts, sodium or potassium borate phosphate salts, and sodium or potassium acetate salts may also be used.

The pH adjuster(s) may be present in an amount needed to adjust the pH of the composition to the desired pH, such as up to about 2%, up to about 1.5%, up to about 1%, up to about 0.75%, up to about 0.5%, up to about 0.25%, or up to about 0.1%, or from about 0.001% to about 2%, from about 0.01% to about 1.5%, or from about 0.01% to about 1% by weight of the composition.

II. Methods of Making and Applying the Compositions

The disclosure also relates to methods of using compositions for, e.g., for decontaminating surfaces by using the compositions disclosed herein. The methods generally comprise mixing the compositions according to the disclosure with a solvent and applying the mixture to a surface. Thus, the disclosure also relates to methods of making decontaminating compositions by diluting the pre-formulated compositions at or near the time of use.

In various embodiments, before applying the mixture to the substrate, the methods may include diluting a pre-formulated product, which may, for example, be in the form of a concentrated solution, emulsion, or dry powder, with a solvent before use. The pre-formulated product may, in various embodiments, be added directly to a solvent or solvent mixture in any manner, and mixed or combined to prepare a composition.

In an embodiment, the hydrogen peroxide is provided in solution form. In a further embodiment, a surfactant composition comprising (a) at least one nonionic surfactant; (b) at least one viscosity modifier; and (c) at least one solvent is mixed with the hydrogen peroxide solution. In an embodiment, the peroxide solution and surfactant solution is mixed just prior to use, such as a few seconds before, about 1, about 5, about 10, about 15, about 20, about 25, about 30, about 35, about 40, about 45, about 50, about 55, or about 60 minutes before the mixture is applied to a substrate. In an embodiment, the peroxide solution and surfactant solution is mixed about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours before it is applied to a substrate.

As used herein, the term "substantially free" or "essentially free" as used herein means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure). Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in a raw material that is included in the composition.

As used herein, "reducing" (and its grammatical variations) means that although something (such as contaminants) may occur or may be present, the occurrence or presence is less than it would have been in the absence of treatment according to methods disclosed herein.

As used herein, "toxic" (and its grammatical variations) means harmful to human, plant or animal health, such as containing or being poisonous material.

As used herein, "corrosive" (and its grammatical variations) means being harmful to a substrate or material, such as being capable of weakening or gradually destroying or damaging said substrate or material.

The term "natural" and "naturally-sourced" means a material of natural origin, such as a material derived from biological organisms, or materials made by natural geological processes. Natural materials can be subsequently chemically or physically modified. In contrast, the term "synthetic" or "artificial" means a material that is not of natural origin. "Bio-based" or "biological" means that the material came from a biological organism. "Plant-based" means that the material came from a plant. "Biodegradable" means capable of being broken down by the action of living things (such as microorganisms).

In this application, the use of the singular includes the plural unless specifically stated otherwise. Thus, the terms "a," "an," and "the" are understood to encompass the plural as well as the singular; thus, "a skin modification stimulus" should be understood to mean "at least one skin modification stimulus" unless expressly stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one unit unless specifically stated otherwise.

The term "and/or" should be understood to include both the conjunctive and the disjunctive and expressly covers instances of either without reference to the other.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%), such as within 9%, 8%, 7%, 6%, 5%, 4%, 3%, 2%, or 1%, according to various embodiments. All numbers (including ratios, concentrations, etc.) disclosed herein are understood to include the term "about" whether or not present. For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. All ranges and amounts given herein are intended to include sub-ranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, +/−1%, +/−0.5%, +/−0.1%, or +/−0.01%.

As used herein, the expressions "ranging from" and "between" are inclusive of the endpoints of the recited range(s).

As used herein, all ranges provided are meant to include every specific range within, and combination of sub ranges between, the given ranges. Thus, a range from 1-5, includes specifically 1, 2, 3, 4, and 5, as well as sub ranges such as 2-5, 3-5, 2-3, 2-4, 1-4, etc. All ranges and values disclosed herein are inclusive and combinable. For example, any value or point described herein that falls within a range described herein can serve as a minimum or maximum value to derive a sub-range, etc.

The term "comprising" (and its grammatical variations) as used herein is used in the inclusive sense of "having" or "including" and not in the exclusive sense of "consisting only of."

Unless otherwise expressly stated, it is in no way intended that any method set forth herein be construed as requiring that its steps be performed in a specific order. Accordingly, where a method claim does not expressly recite an order to be followed by its steps or it is not specifically stated in the claims or descriptions that the steps are to be limited to a specific order, it is no way intended that any particular order be inferred.

The compositions and methods of the present disclosure can comprise, consist of, or consist essentially of the essential elements and limitations of the disclosure described herein, as well as any additional or optional ingredients, components, or limitations described herein or otherwise useful.

Several embodiments having been described above; the disclosure may be better understood by reference to examples. The following examples are intended for illustration purposes only and should not be construed as limiting in any way.

EXAMPLES

The following Example is intended to be non-limiting and explanatory in nature only. In the Example, amounts are expressed in percentage by weight (wt %) of materials, relative to the total weight of the composition, unless otherwise indicated.

Example 1—Biological Decontamination Efficacy Evaluation

Inventive Compositions 1 and 2 were prepared according to the formulations set forth in Table 1.

TABLE 1

COMPOSITIONS

| | Inventive Composition 1 | Inventive Composition 2 |
|---|---|---|
| Xanthan Gum | 0.50136 g | 0.50278 g |
| Levulinic Acid | 0.31569 g | 0.32113 g |
| Ethyl Lactate | 0.72927 g | 0.72724 g |
| TWEEN 80 | 0.08097 g | 0.09844 g |
| Source of Hydrogen Peroxide | 160 g UHP (urea) dissolved in 1 L DI $H_2O$ | 4% $H_2O_2$ Solution |

Inventive Composition 1 was prepared by homogenizing 0.50136 g xanthan gum, 0.31569 g levulinic acid, 0.72927 g ethyl lactate, and 0.08097 g TWEEN 80 in a solution of 160 g UHP and dissolving the solution in 1 L DI $H_2O$ immediately prior to use. Inventive Composition 2 was prepared by homogenizing 0.50278 g xanthan gum, 0.32113 g levulinic acid, 0.72724 g ethyl lactate, and 0.09844 g TWEEN 80 in a 4% $H_2O_2$ solution.

Figure 2:
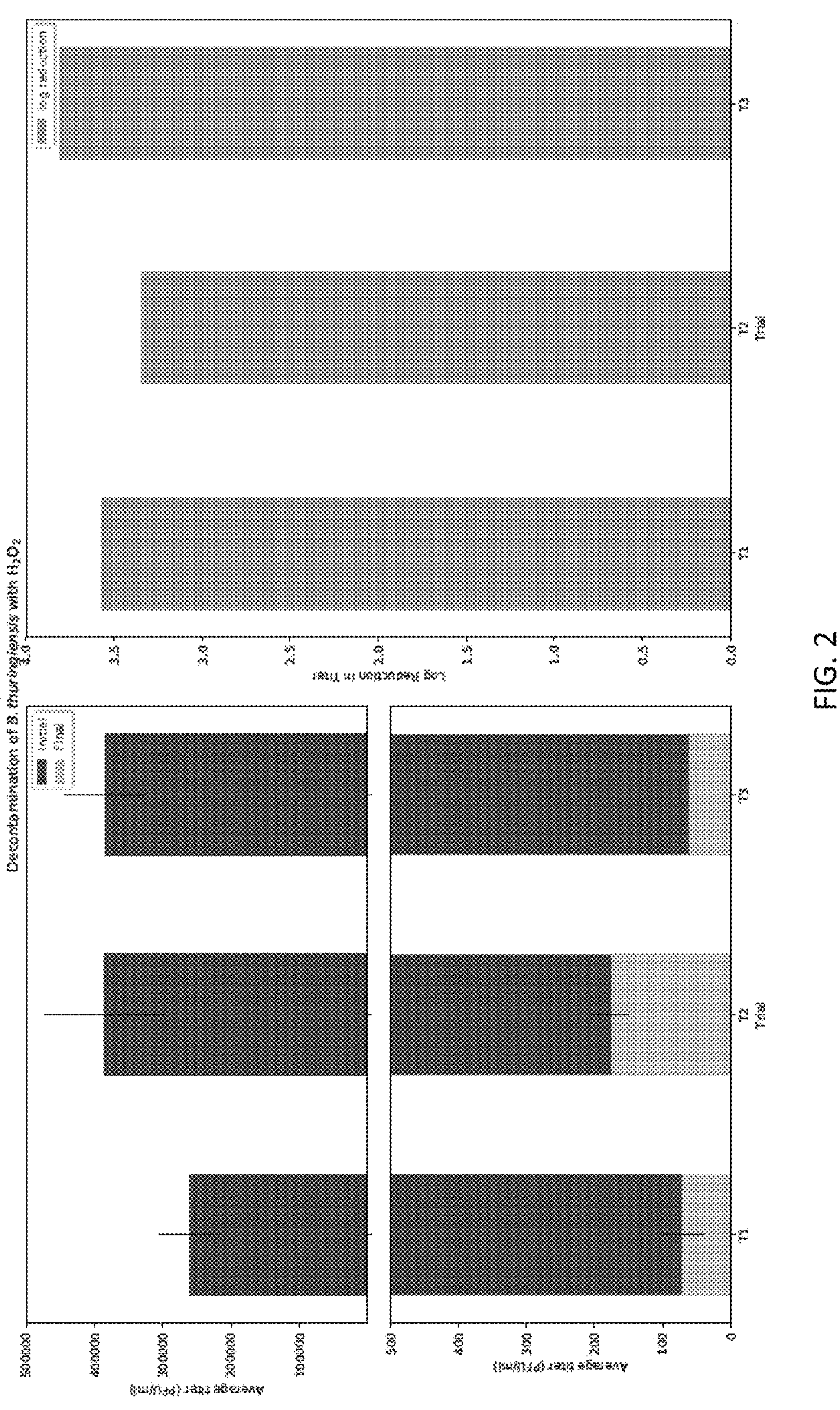
FIG. 2 shows diagrams illustrating titer and log reduction of *B. thuringiensis* after contact with $H_2O_2$-based compositions.

An inoculum of $1\times10^9$ CFU/mL *Bacillus thuringiensis* spores was applied to 4 inch by 4-inch glass coupons using a 6 jet Collison nebulizer. The inoculum was aerosolized for 45 minutes using clean, dry air at 20 psi and assisted with two small fans inside an 8-foot by 8-foot chamber. An hour settling time was allowed prior to swabbing three coupons to determine a baseline coverage. Inventive Composition 1 and Inventive Composition 2 were applied using a Createch Tri-Jet Fogger for 20 seconds, then allowed to settle for 2 hours prior to swabbing three coupons. Each swab was enumerated in triplicate. Final microorganism counts were graphed in FIGS. 1 and 2 and the raw data is disclosed in Tables 2 and 3 below.

TABLE 2

EFFICACY TEST OF $H_2O_2$-BASED CANDIDATE SOLUTIONS FOR INACTIVATION OF $1.61 \times 10^9$ CFU/ML *B. THURINGIENSIS*

| Sample | Dilution | Plaque counts | Titer | Average Titer |
|---|---|---|---|---|
| Pre 1 | −3 | 189 | $1.89 \times 10^5$ | $2.36 \times 10^5$ |
| | −4 | 22 | $2.20 \times 10^5$ | |
| | −5 | 3 | $3.00 \times 10^5$ | |
| Pre 2 | −3 | 393 | $3.93 \times 10^5$ | $4.08 \times 10^5$ |
| | −4 | 43 | $4.30 \times 10^5$ | |
| | −5 | 4 | $4.00 \times 10^5$ | |
| Pre 3 | −3 | 840 | $8.40 \times 10^5$ | $9.70 \times 10^5$ |
| | −4 | 87 | $8.7 \times 10^5$ | |
| | −5 | 12 | $1.20 \times 10^5$ | |
| Post 1 | −1 | 2 | $2.00 \times 10^1$ | $2.00 \times 10^1$ |
| | −2 | 0 | 0 | |
| Post 2 | −1 | 4 | $4.00 \times 10^1$ | $7.00 \times 10^1$ |
| | −2 | 1 | $1.00 \times 10^2$ | |
| Post 3 | −1 | 12 | $1.2 \times 10^2$ | $1.10 \times 10^2$ |
| | −2 | 1 | $1.00 \times 10^2$ | |

TABLE 3

EFFICACY TEST OF $H_2O_2$-BASED CANDIDATE SOLUTIONS FOR INACTIVATION OF $1.14 \times 10^9$ CFU/ML *B. THURINGIENSIS*

| Sample | Dilution | Plaque counts | Titer | Average Titer |
|---|---|---|---|---|
| Pre 1 | −3 | 268 | $2.68 \times 10^5$ | $2.59 \times 10^5$ |
| | −4 | 31 | $3.10 \times 10^5$ | |
| | −5 | 2 | $2.00 \times 10^5$ | |
| Pre 2 | −3 | 368 | $3.68 \times 10^5$ | $3.86 \times 10^5$ |
| | −4 | 29 | $2.90 \times 10^5$ | |
| | −5 | 5 | $5.00 \times 10^5$ | |
| Pre 3 | −3 | 424 | $4.24 \times 10^5$ | $3.85 \times 10^5$ |
| | −4 | 43 | $4.30 \times 10^5$ | |
| | −5 | 3 | $3.00 \times 10^5$ | |
| Post 1 | −1 | 4 | $4.00 \times 10^1$ | $7.00 \times 10^1$ |
| | −2 | 1 | $1.00 \times 10^2$ | |
| Post 2 | −1 | 15 | $1.50 \times 10^2$ | $1.75 \times 10^2$ |
| | −2 | 2 | $2.00 \times 10^2$ | |
| Post 3 | −1 | 6 | $6.00 \times 10^1$ | $6.00 \times 10^1$ |
| | −2 | 0 | 0 | |

The biological decontamination efficacy of Inventive Composition 1 and Inventive Composition 2 was evaluated. Efficacy tests using the developed decontaminant with UHP and aqueous hydrogen peroxide resulted in a 4-log reduction of surrogate microorganisms. The residue formed by urea after application could be safely removed from surfaces. The final decontaminant comprising the 4% hydrogen peroxide solution did not leave a visible residue.

What is claimed is:

1. A decontaminating composition comprising a mixture of a peroxide solution and a surfactant composition, wherein (i) the surfactant composition comprises:

(a) from about 20% to about 40% xanthan gum, (b) from about 10% to about 25% levulinic acid, (c) from about 32% to about 63% ethyl lactate, and (d) from about 3% to about 7% polyoxyethylene (20) sorbitan monooleate, wherein all weights are relative to the total weight of the surfactant composition, (ii) the peroxide solution comprises from about 1% to about 12% hydrogen peroxide, and the mixture comprises from about 0.001 g to about 10 g of the surfactant composition per liter of the peroxide solution.

2. The decontaminating composition of claim 1, wherein the surfactant composition comprises from about 25% to about 35% by weight xanthan gum, relative to the total weight of the surfactant composition.

3. The decontaminating composition of claim 1, wherein the surfactant composition comprises from about 15% to about 23% by weight levulinic acid, relative to the total weight of the surfactant composition.

4. The decontaminating composition of claim 1, wherein the surfactant composition comprises from about 40% to about 50% by weight ethyl lactate, relative to the total weight of the surfactant composition.

5. The decontaminating composition of claim 1, wherein the surfactant composition comprises from about 4% to about 6% by weight polyoxyethylene (20) sorbitan monooleate, relative to the total weight of the surfactant composition.

6. The decontaminating composition of claim 1, wherein the pH of the mixture is basic.

7. The decontaminating composition of claim 1, wherein (i) the surfactant composition comprises:

(a) from about 25% to about 35% xanthan gum, (b) from about 15% to about 23% levulinic acid, (c) from about 40% to about 50% ethyl lactate, and (d) from about 4% to about 6% polyoxyethylene (20) sorbitan monooleate, wherein all weights are relative to the total weight of the surfactant composition, (ii) the peroxide solution comprises from about 2% to about 8% hydrogen peroxide, and the mixture comprises from about 0.1 g to about 4 g of the surfactant composition per liter of the peroxide solution.

8. A method of decontaminating a substrate, comprising:

(A) mixing a peroxide solution with a surfactant composition, wherein (i) the surfactant composition comprises:

(a) from about 20% to about 40% xanthan gum, (b) from about 10% to about 25% levulinic acid, (c) from about 32% to about 63% ethyl lactate, and (d) from about 3% to about 7% polyoxyethylene (20) sorbitan monooleate, wherein all weights are relative to the total weight of the surfactant composition, (ii) the peroxide solution comprises from about 1% to about 12% hydrogen peroxide, and the mixture comprises from about 0.001 g to about 10 g of the surfactant composition per liter of the peroxide solution; and (B) applying the mixture to a substrate.

9. The method of claim 8, wherein the surfactant composition comprises from about 25% to about 35% by weight xanthan gum, relative to the total weight of the surfactant composition.

10. The method of claim 8, wherein the surfactant composition comprises from about 15% to about 23% by weight levulinic acid, relative to the total weight of the surfactant composition.

11. The method of claim 8, wherein the surfactant composition comprises from about 40% to about 50% by weight ethyl lactate, relative to the total weight of the surfactant composition.

12. The method of claim 8, wherein the surfactant composition comprises from about 4% to about 6% by weight polyoxyethylene (20) sorbitan monooleate, relative to the total weight of the surfactant composition.

13. The method of claim 8, wherein the pH of the mixture is basic.

14. The method of claim 8, wherein (i) the surfactant composition comprises:

(a) from about 25% to about 35% xanthan gum, (b) from about 15% to about 23% levulinic acid, (c) from about 40% to about 50% ethyl lactate, and (d) from about 4% to about 6% polyoxyethylene (20) sorbitan monooleate, wherein all weights are relative to the total weight of the surfactant composition, (ii) the peroxide solution comprises from about 2% to about 8% hydrogen peroxide, and the mixture comprises from about 0.1 g to about 4 g of the surfactant composition per liter of the peroxide solution.

15. A method of making a decontaminating composition comprising mixing a peroxide solution with a surfactant composition, wherein (i) the surfactant composition comprises:

(a) from about 20% to about 40% xanthan gum, (b) from about 10% to about 25% levulinic acid, (c) from about 32% to about 63% ethyl lactate, and (d) from about 3% to about 7% polyoxyethylene (20) sorbitan monooleate, wherein all weights are relative to the total weight of the surfactant composition, (ii) the peroxide solution comprises from about 1% to about 12% hydrogen peroxide, and the mixture comprises from about 0.001 g to about 10 g of the surfactant composition per liter of the peroxide solution.

16. The method of claim 15, wherein pH of the mixture is basic.

17. The method of claim 15, wherein the surfactant composition comprises from about 25% to about 35% by weight xanthan gum, relative to the total weight of the surfactant composition.

18. The method of claim 15, wherein the surfactant composition comprises from about 15% to about 23% by weight levulinic acid, relative to the total weight of the surfactant composition.

19. The method of claim 15, wherein the surfactant composition comprises from about 40% to about 50% by weight ethyl lactate, relative to the total weight of the surfactant composition.

20. The method of claim 15, wherein (i) the surfactant composition comprises:

(a) from about 25% to about 35% xanthan gum, (b) from about 15% to about 23% levulinic acid, (c) from about 40% to about 50% ethyl lactate, and (d) from about 4% to about 6% polyoxyethylene (20) sorbitan monooleate, wherein all weights are relative to the total weight of the surfactant composition, (ii) the peroxide solution comprises from about 2% to about 8% hydrogen peroxide, and the mixture comprises from about 0.1 g to about 4 g of the surfactant composition per liter of the peroxide solution.

* * * * *